(12) United States Patent
Hughes et al.

(10) Patent No.: US 6,350,751 B1
(45) Date of Patent: Feb. 26, 2002

(54) THERAPEUTIC AGENTS

(75) Inventors: Michael L. Hughes, Kingsdown Deal; Richard A Storey, Chartham, both of (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/657,202

(22) Filed: Sep. 7, 2000

Related U.S. Application Data

(60) Provisional application No. 60/168,083, filed on Nov. 30, 1999.

(30) Foreign Application Priority Data

Oct. 11, 1999 (GB) .............................. 9923968

(51) Int. Cl.[7] .................... C07D 487/04; A61K 31/519; A61P 9/00
(52) U.S. Cl. .................. 514/252.16; 544/262
(58) Field of Search ............................ 514/258, 252.16; 544/262

(56) References Cited

U.S. PATENT DOCUMENTS 6,251,904 B1 * 6/2001 Bunnage et al. ......... 514/252.6

FOREIGN PATENT DOCUMENTS

| WO | WO9849166 | 11/1998 |
| WO | WO9954333 | 10/1999 |

OTHER PUBLICATIONS

Gautam R. Desiraju, J. Chem. Soc., Chem. Commun., 1991 Issue 6, 426–428, "Hydration in Organic Crystals: Prediction from Molecular Structure".

\* cited by examiner

*Primary Examiner*—Bruck Kifle
*Assistant Examiner*—Thomas McKenzie
(74) *Attorney, Agent, or Firm*—Peter C. Richardson; Gregg C. Benson; Arlene K. Musser

(57) ABSTRACT

The invention relates anhydrous para-toluenesulphonic acid salts of 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo [4,3-d]pyrimidin-7-one having the formula (I):

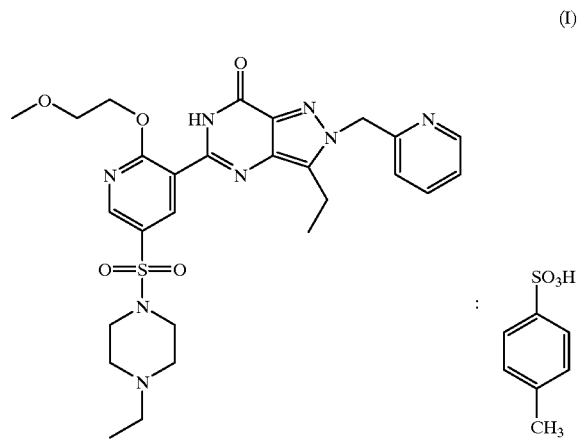

a process for preparing compounds (I), pharmaceutical compositions containing (I) and use of (I) in medicine.

6 Claims, No Drawings

THERAPEUTIC AGENTS

This application claims priority from U.K. Application 9923968.3 filed Oct. 11, 1999 and U.S. provisional application Ser. No. 60/168,083 filed on Nov. 30, 1999.

The present invention relates to pharmaceutically acceptable anhydrous paratoluene sulphonic acid salts of 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo [4,3-d]pyrimidin-7-one having the formula (I):

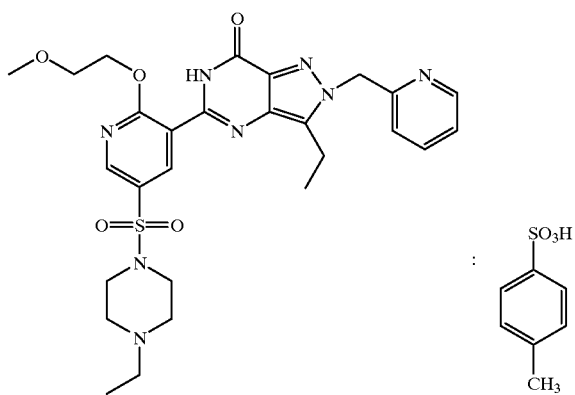

In addition the present invention relates to pharmaceutical compositions containing anhydrous para-toluene sulphonic acid salts of 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo [14,3-d] pyrimidin-7-one, to processes for the preparation of (I) and uses of (I) in medicine.

3-Ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo[4,3-d]pyrimidin-7-one has been disclosed (as Example 4) and claimed in published international application WO99/54333, international publication date 28$^{th}$ Oct. 1999. As detailed in WO99/54333 compounds of this type are especially useful in the treatment of inter alia male erectile dysfunction. WO99/54333 in its entirety and in particular the description of general processes for the preparation of 3-Ethyl-5-[5-(4-ethylpiperazin-1-ylsulphonyl)-2-(2-methoxy ethoxy) pyridin-3-yl]-2-(pyridin-2-yl)methyl-2,6-dihydro-7H-pyrazolo[4,3-d] pyrimidin-7-one is incorporated herein by reference.

For successful utility within the pharmaceutical industry it is critical that the properties of an active material are either known or can be reasonably predicted throughout the necessary processes during both its manufacture and pharmaceutical processing as well as during its shipping, storage and eventual therapeutic use. In some cases compounds can exhibit desirable medicinal properties which cannot be translated directly into a suitable pharmaceutical composition because the active compound itself has unsatisfactory physical properties such as for example poor processing stability or low solubility.

Thus the challenge facing the pharmaceutical chemist in the search for new and improved drug compounds is not only the manufacture, isolation and characterisation of new drug compounds as well as the determination of their particular medicinal properties but also the provision of suitable pharmaceutically acceptable salts of such compounds.

The problem addressed by the present invention is the provision of a pharmaceutically acceptable salt of 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo [4,3-d]pyrimidin-7-one which can be efficiently processed to provide stable and effective formulations of the drug, an in particular solid and compressible dosage forms of the drug. Such dosage forms include conventional-release oral tablets, controlled-release (matrix) tablets, fast-dissolving formulations, sub-lingual tablets, buccal tablets, oral powder, soft gel and granule filled capsules, powders for reconstituted suspensions, conventional and controlled-release multi-particulate systems filled into capsules or compressed into tablets, lozenges, dragees, suppositories, pessaries, solid implants, lyophile plugs, nanoparticles and microparticles and powder for suspension and nasal delivery, and dry inhalation systems. Additional suitable dosage forms and routes of potential administration are discussed in detail in the formulation section herein.

Important criteria to be satisfied are, inter alia, that the pharmaceutically acceptable salt should be crystalline, non-hygroscopic, of suitable melting point (preferably a melting point of at least about 100°, more preferably greater than about 150° C.), possess chemical stability across a range of temperature and humidity conditions, have acceptable solubility, have an acceptable (preferably a rapid and complete) dissolution profile, have acceptable mechanical properties such as for example exhibit good compressibility without exhibiting polymorphism.

In the search for a pharmaceutically acceptable salt of 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo [4,3-d]pyrimidin-7-one several potential salts have been investigated. However of these, only one salt, the para-toluene sulphonic acid salt was found to fulfil the necessary criteria for a pharmaceutically acceptable salt.

Hydrated salts can provide particular issues in processing, especially during for example the milling and/or drying stages. It has been disclosed that the tendency of organic molecules to hydrate can be predicted from their molecular structure, "Hydration in organic crystals: prediction from molecular structure", Desiraju, Gautam R. Sch. Chem., Univ. Hyderabad, Hyderabad, 500 134, India. J. Chem. Soc., Chem. Commun. (1991), Issue 6, 426–8. CODEN: JCCCAT; ISSN: 0022–4936. (EN) CAN 114:237859. Using such a predictive method it would be predicted that the tosylate salt of 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo [4,3-d]pyrimidin-7-one would indeed be highly likely to hydrate. Several of the salts investigated form hydrates. Furthermore, corresponding experiments on the structurally similar besylate salt of 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo [4,3-d]pyrimidin-7-one have determined that in addition to at least 5 anhydrous polymorphs a hydrated polymorph of the besylate salt is indeed formed.

The problem of selecting a pharmaceutically acceptable salt form for 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo[4,3-d]pyrimidin-7-one has been solved by the surprising finding that the anhydrous para-toluene sulphonate salt of formula (I) meets the above criteria for a pharmaceutically acceptable salt. Even more surprising is the finding that the para-toluenesulphonate salt of the present invention does not appear to form crystalline hydrates under a range of conditions. This is particularly surprising as initial predictions would indicate that the toslyate salt would form a hydrate, especially given the fact that the besylate salt and other salts investigated hydrated as predicted. Furthermore the anhydrous para-toluene sulphonate salt of the present invention exhibits good physical dosage form stability, demonstrates stability during drying and milling processes and has a desirable drug substance stability profile.

An additional advantage of the anhydrous para-toluenesulphonate salt of the present invention versus the corresponding besylate salt in particular is that it can be prepared in improved yield (98.5% versus 85%). A further additional advantage of the particular salt of the present invention is that ease of processing of the para toluene sulphonic acid counter ion versus for example the benzene sulphonic acid (for the besylate salt).

Thus it has now been established that because of its uniquely favourable combination of pharmaceutical properties, the anhydrous para-toluene sulphonate salt of 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo [4,3-d]pyrimidin-7-one is especially suitable for pharmaceutical formulation and is the preferred form for administration to humans.

The term anhydrous salt as defined herein means that there is no bound water within the crystal lattice structure i.e. the compound cannot form a crystalline hydrate. For the avoidance of doubt it is to be understood that surface water i.e. water found upon the surface of a crystal is not bound water.

The preparation of the anhydrous para-toluene sulphonate salt of 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo [4,3-d]pyrimidin-7-one may be carried out as illustrated in the Example hereinafter.

The compound of the invention, pharmaceutically acceptable salts, and pharmaceutically acceptable solvates thereof can be administered alone but, in human therapy will generally be administered in admixture with a suitable pharmaceutical excipient diluent or carrier selected with regard to the intended route of administration and standard pharmaceutical practice.

For example, the compound of the invention or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, sustained-, controlled-release or pulsatile delivery applications. The compound of the invention may also be administered via intracavernosal injection. The compound of the invention may also be administered via fast dispersing or fast dissolving dosages forms.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol.

The compound of the invention can also be administered parenterally, for example, intracavernosally, intravenously, intra-arterially, intraperitoneally, intrathecally, intraventricularly, intraurethrally intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compound of the invention or salts or solvates thereof will usually be from 10 to 500 mg (in single or divided doses).

Thus, for example, tablets or capsules of the compound of the invention or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including MED and FSD), the compound of the invention may be taken as a single dose on an "as required" basis (i.e. as needed or desired).

The compound of the invention can also be administered intranasally or by inhalation and can be conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the compound of the invention and a suitable powder base such as lactose or starch.

Aerosol or dry powder formulations are preferably arranged so that each metered dose or "puff" contains from 1 to 50 mg of compound of the invention for delivery to the patient. The overall daily dose with an aerosol will be in the range of from 1 to 50 mg which may be administered in a single dose or, more usually, in divided doses throughout the day.

The compound of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compound of the invention or salts or solvates thereof can be administered in the form of a suppository or pessary, or they may be applied topically in the form of a gel, hydrogel lotion, solution, cream, ointment or dusting powder. The compound of the invention or salts or solvates thereof may also be dermally administered. The compound of the invention or salts or solvates thereof may also be transdermally administered, for example, by the use of a skin patch. The compound may also be administered by the ocular, pulmonary or rectal routes.

For ophthalmic use, the compound can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, the compound may be formulated in an ointment such as petrolatum.

For application topically to the skin, the compound of the invention or salts or solvates thereof can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyidodecanol, benzyl alcohol and water.

The compound of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma- cyclodextrins are most commonly used and suitable examples are described in WO-A-91/11172, WO-A-94/02518 and WO-A-98/55148.

Example Tablet Formulation

In general a formulation of the p-tosylate salt tablet could typically contain between about 5mg and 400mg of active compound whilst tablet fill weights may range from 50mg to 1000mg. An example formulation for a 25mg tablet is illustrated:

| Ingredient | % w/w |
| --- | --- |
| p-tosylate salt | 32.383* |
| Microcrystalline Cellulose | 42.117 |
| Dibasic Calcium Phosphate, anhydrous | 21.000 |
| Sodium Starch Glycollate | 3.000 |
| Magnesium Stearate | 1.500 |

*Quantity adjusted in accordance with drug activity.

The tablets will be manufactured by a standard process, for example, direct compression or a wet or dry granulation process. The tablet cores may be coated with an appropriate overcoat.

Generally, in humans, oral administration of the compound of the invention is the preferred route, being the most convenient and, for example in MED, avoiding the well-known disadvantages associated with intracavernosal (i.c.) administration. A preferred oral dosing regimen in MED for a typical man is from 25 to 250 mg of compound when required. In circumstances where the recipient suffers from a swallowing disorder or from impairment of drug absorption after oral administration, the drug may be administered parenterally, sublingually or buccally.

For veterinary use, the compound of the present invention is administered as a suitably acceptable formulation in accordance with normal veterinary practice and the veterinary surgeon will determine the dosing regimen and route of administration which will be most appropriate for a particular animal.

Thus the invention provides a pharmaceutical composition comprising the compound of the present invention, or a pharmaceutically acceptable solvate or pro-drug thereof, together with a pharmaceutically acceptable diluent or carrier.

It further provide s a veterinary formulation comprising the compound of the present invention, or a veterinarily acceptable solvate or pro-drug thereof, together with a veterinarily acceptable diluent or carrier.

The invention also provides the compound of the present invention, or a pharmaceutically acceptable solvate or pro-drug thereof, or a pharmaceutical composition containing any of the foregoing, for use as a human medicament.

In addition, it provides the compound of the present invention, or a veterinarily acceptable solvate or pro-drug thereof, or a veterinary formulation containing any of the foregoing, for use as an animal medicament.

In yet another aspect, the invention provides the use of a compound of the present invention, or a pharmaceutically acceptable solvate or pro-drug thereof, for the manufacture of a human medicament for the curative or prophylactic treatment of a medical condition for which a cGMP PDE5 inhibitor is indicated. There is further provided the use of the compound of the present invention, solvate or pro-drug thereof, in the manufacture of a medicament for the treatment of a medical condition in which inhibition of a cGMP PDE5 is desirable.

It also provides the use of the compound of the present invention, or a veterinarily acceptable solvate or pro-drug thereof, for the manufacture of an animal medicament for the curative or prophylactic treatment of a medical condition for which a cGMP PDE5 inhibitor is indicated.

Moreover, the invention provides the use of the compound of the present invention, or a pharmaceutically acceptable solvate or pro-drug thereof, for the manufacture of a human medicament for the curative or prophylactic treatment of mammalian sexual dysfunctions, male erectile dysfunction (MED), impotence, female sexual dysfunction (FSD), clitoral dysfunction, female hypoactive sexual desire disorder, female sexual arousal disorder, female sexual pain disorder, female sexual orgasmic dysfunction (FSOD), sexual dysfunction due to spinal cord injury, selective serotonin re-uptake inhibitor (SSRI) induced sexual dysfunction, premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, peripheral vascular disease, stroke, nitrate induced tolerance, bronchitis, allergic asthma, chronic asthma, allergic rhinitis, diseases and conditions of the eye, diseases characterised by disorders of gut motility, pre-eclampsia, Kawasaki's syndrome, nitrate tolerance, multiple sclerosis, diabetic nephropathy, peripheral diabetic neuropathy, Alzheimer's disease, acute respiratory failure, psoriasis, skin necrosis, cancer, metastasis, baldness, nutcracker oesophagus, anal fissure, haemorrhoids, hypoxic vasoconstriction or blood pressure stabilisation of during haemodialysis. Particularly preferred conditions include MED and FSD.

It also provides the use of the compound of the present invention, or a veterinarily acceptable solvate or pro-drug thereof, for the manufacture of an animal medicament for the curative or prophylactic treatment of mammalian sexual dysfunctions, male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD), sexual dysfunction due to spinal cord injury, premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, e.g. post-percutaneous transluminal coronary angioplasty (post-PTCA), peripheral vascular disease, stroke, nitrate induced tolerance, bronchitis, allergic asthma, chronic asthma, allergic rhinitis, glaucoma, diseases characterised by disorders of gut motility, e.g. irritable bowel syndrome (IBS), pre-eclampsia, Kawasaki's syndrome, nitrate tolerance, multiple sclerosis, diabetic nephropathy, peripheral diabetic neuropathy, Alzheimers disease, acute respiratory failure, psoriasis, skin necrosis, cancer, metastasis, baldness, nutcracker oesophagus, anal fissure, haemorrhoids or hypoxic vasoconstriction. Particularly preferred conditions include MED and FSD.

Additionally, the invention provides a method of treating or preventing a medical condition for which a cGMP PDE5 inhibitor is indicated, in a mammal (including a human being), which comprises administering to said mammal a therapeutically effective amount of the compound of the present invention, or a pharmaceutically or veterinarily acceptable solvate or pro-drug thereof, or a pharmaceutical composition or veterinary formulation containing any of the foregoing.

Still further, the invention provides a method of treating or preventing mammalian sexual dysfunctions, male erectile dysfunction (MED), impotence, female sexual dysfunction (FSD), clitoral dysfunction, female hypoactive sexual desire disorder, female sexual arousal disorder, female sexual pain disorder, female sexual orgasmic dysfunction (FSOD), sexual dysfunction due to spinal cord injury, premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, e.g. post-percutaneous transluminal coronary angioplasty (post-PTCA), peripheral vascular disease, stroke, nitrate induced tolerance, bronchitis, allergic asthma, chronic asthma, allergic rhinitis, glaucoma, diseases characterised by disorders of gut motility, e.g. irritable bowel syndrome (IBS), pre-eclampsia, Kawasaki's syndrome, nitrate tolerance, multiple sclerosis, diabetic nephropathy, peripheral diabetic neuropathy, Alzheimer's disease, acute respiratory failure, psoriasis, skin necrosis, cancer, metastasis, baldness, nutcracker oesophagus, anal fissure, haemorrhoids or hypoxic vasoconstriction in a mammal (including a human being), which comprises administering to said mammal a therapeutically effective amount of the compound of the present invention, or a pharmaceutically or veterinarily acceptable solvate or pro-drug thereof, or a pharmaceutical composition or veterinary formulation containing any of the foregoing.

In a yet further aspect of the present invention provides a combination of the compound of the present invention with further compounds useful in the inhibition of $PDE_5$ wherein said combination is useful for the treatment or prevention of mammalian sexual dysfunctions such as male erectile dysfunction (MED), impotence, female sexual dysfunction (FSD), clitoral dysfunction, female hypoactive sexual desire disorder, female sexual arousal disorder, female sexual pain disorder, female sexual orgasmic dysfunction (FSOD), sexual dysfunction due to spinal cord injury, premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, e.g. post-percutaneous transluminal coronary angioplasty (post-PTCA), peripheral vascular disease, stroke, nitrate induced tolerance, bronchitis, allergic asthma, chronic asthma, allergic rhinitis, glaucoma, diseases characterised by disorders of gut motility, e.g. irritable bowel syndrome (IBS), pre-eclampsia, Kawasaki's syndrome, nitrate tolerance, multiple sclerosis, diabetic nephropathy, peripheral diabetic neuropathy, Alzheimer's disease, acute respiratory failure, psoriasis, skin necrosis, cancer, metastasis, baldness, nutcracker oesophagus, anal fissure, haemorrhoids or hypoxic vasoconstriction in a mammal (including a human being).

EXAMPLE 1

4-{6-Ethoxy-5-[3-ethyl-6,7-dihydro-7-oxo-2-(2-pyridylmethyl)-2H-pyrazolo[4,3-d]pyrimidin-5-yl]-3-pyridylsulfonyl}-1-ethylpiperazine para-toluenesulfonate also named as (Para-toluene sulphonate salt of 3-Ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo[4,3-d]pyrimidin-7-one)

4-{6-Ethoxy-5-[3-ethyl-6,7-dihydro-7-oxo-2-(2-pyridylmethyl)-2H-pyrazolo[4,3-d]pyrimidin-5-yl]-3-pyridylsulfonyl}1-ethylpiperazine (100 g, 0.16 mol) was heated in 2-butanone/6.0% water (600 mL) to 50° C. yielding a pale yellow solution. The reaction mixture was heated to azetropically distil of 160 ml of solvent to remove water. The distilled solution was warmed to 60° C. and the acid solution of p-toluenesulfonic acid monohydrate (31.11 g, 0.16 mol) dissolved in 2-butanone (140 mL) was added over an hour. During the addition of the acid slow crystallisation was observed. The reaction mixture was slowly cooled from 60° C. to 0–5° C. over three hours, and stirred for a further hour, then filtered off the solid, washed with 2-butanone (200 mL) and dried under vacuum at 50° C. to afford the title compound (116 g, 93.7%) as a white solid. Mpt 240° C. (DMSO$_{d6}$): 1.20 (6H, m), 2.23 (3H, st), 2.75 (2H, m), 2.97 (2H, q), 3.18 (4H, m), 3.35 (3H, s), 3.55 (2H, m), 3.68 (2H, m), 3.83 (2H, m), 4.59 (2H, m), 5.70 (2H, s), 7.08 (2H, d), 7.20 (1H, d), 7.34 (1H, m), 7.43 (2H, d), 7.80 (1H, m), 8.35 (1H, d), 8.70 (1H, d), 8.74 (1H, d). Single X-ray crystallography data demonstrated the proposed structure was correct. Mpt quoted +/–5° C. preferably +/–2° C. Experiments have shown that under certain conditions at least two further polymorphs of (I) can be detected via differential scanning calorimetry (DSC). Additional experiments have shown that on re-slurrying in a mixture of methyl ethyl ketone and water these further polymorphs can be converted to the compound of Example 1.

PREPARATION 1

4-amino-5-ethyl-1-(2-pyridylmethyl)-1H-pyrazole-3-carboxamide (1a) Ethyl 3-ethyl-1H-pyrazole-5-carboxylate Ethanolic sodium ethoxide solution (21% w/w; 143 ml, 0.39 mol) was added dropwise to a stirred, ice-cooled solution of diethyl oxalate (59.8 ml, 0.44 mol) in absolute ethanol (200 ml) under nitrogen and the resulting solution stirred for 15 minutes. Butan-2-one (39 ml, 0.44 mol) was then added dropwise, the cooling bath removed, the reaction mixture stirred for 18 hours at room temperature and then for 6 hours at 40° C., then the cooling bath reintroduced. Next, glacial acetic acid (25 ml, 0.44 mol) was added dropwise, the resulting solution stirred for 30 minutes at 0° C., hydrazine hydrate (20 ml, 0.44 mol) added dropwise, then the reaction mixture allowed to warm to room temperature and maintained there over a period of 18 hours, before being evaporated under reduced pressure. The residue was partitioned between dichloromethane (300 ml) and water (100 ml), then the organic phase separated, washed with water (2×100 ml), dried (Na$_2$SO$_4$) and concentrated under reduced pressure to give the title compound (66.0 g). δ (CDCl$_3$): 1.04 (3H,t), 1.16 (3H,t), 2.70 (2H,q), 4.36 (2H,q), 6.60 (1H,s). LRMS: m/z 169 (M+1)$^+$.

(1b) 3-Ethyl-1 H-pyrazole-5-carboxylic acid

Aqueous sodium hydroxide solution (10M; 100 ml, 1.0 mol) was added dropwise to a stirred suspension of the title compound of example (4a) (66.0 g, 0.39 mol) in methanol and the resulting solution heated under reflux for 4 hours. The cool reaction mixture was concentrated under reduced pressure to ca. 200 ml, diluted with water (200 ml) and this mixture washed with toluene (3×100 ml). The resulting aqueous phase was acidified with concentrated hydrochloric acid to pH 4 and the white precipitate collected and dried by suction to provide the title compound (34.1 g). δ (DMSO$_{d6}$): 1.13 (3H,t), 2.56 (2H,q), 6.42 (1H,s).

(1c) 3-Ethyl-4-nitro-1H-pyrazole-5-carboxylic acid

Fuming sulphuric acid (17.8 ml) was added dropwise to stirred, ice-cooled fuming nitric acid (16.0 ml), the resulting solution heated to 50° C., 3-ethyl-1H-pyrazole-5-carboxylic acid added portionwise over 30 minutes whilst maintaining the reaction temperature below 60° C. The resulting solution was heated for 18 hours at 60° C., allowed to cool, then poured onto ice. The title compound was obtained as a brown solid (64%). δ (DMSO$_{d6}$): 1.18 (3H,t), 2.84 (2H,m), 13.72 (1H,s).

(1d) 3-Ethyl-4-nitro-1H-pyrazole-5-carboxamide

A solution of the title compound of example (4c) (15.4 g, 0.077 mol) in thionylchloride (75 ml) was heated under reflux for 3 hours and then the cool reaction mixture evaporated under reduced pressure. The residue was azeotroped with tetrahydrofuran (2×50 ml) and subsequently suspended in tetrahydrofuran (50 ml), then the stirred suspension ice-cooled and treated with gaseous ammonia for 1 hour. Water (50 ml) was added and the resulting mixture evaporated under reduced pressure to give a solid which, after trituration with water and drying by suction, furnished the title compound as a white solid (90%). δ (DMSO$_{d6}$): 1.17 (3H,t), 2.87 (2H,m), 7.40 (1H,s), 7.60 (1H,s), 7.90 (1H,s). LRMS: m/z 185 (M+1)$^+$.

(1e) 5-Ethyl-4-nitro-1-(2-pyridylmethyl)-1H-pyrazole-3-carboxamide.

Caesium carbonate (1.414 kg, 4.34 mol) was added to a suspension of the title compound of example (4d) (800 g, 4.34 mol) in acetonitrile (5l) and the mixture warmed to 60° C. 2-Chloromethylpyridine (664.7 g, 5.23 mol) was added and the reaction heated at 70° C. for 7 hours, then water (9.5l) added and the reaction mixture cooled to 10° C. Granulation of this mixture gave a precipitate which was filtered and dried to afford 3-ethyl4-nitro-1-(pyridin-2-yl) methyl-pyrazole-5-carboxamide (367 g). Sodium chloride (1.58 kg) was added to the filtrate and the solution extracted with ethyl acetate (4×1.75l). The combined organic extracts were distilled to remove approximately 10 l of solvent, toluene (5.6l) added over 35 minutes to the hot (69–76° C.) solution and the mixture allowed to cool. The resulting suspension was granulated at <10° C. for 30 minutes, filtered, the solid washed with ethyl acetate:toluene (50:50) 600 ml) and dried (60° C.) to afford the title compound (624 g 52%) as a light brown solid. δ (DMSO$_{d6}$): 1.08 (3H,t), 3.02 (2H,q), 5.53 (2H,s), 7.34 (2H,m), 7.65 (1H,s), 7.82 (1H,m), 7.93 (1H,s), 8.52 (1H,d). LRMS: m/z 276 (M+1)$^+$.

(1f) 4-Amino-5-ethyl-1-(2-pyridylmethyl)-1H-pyrazole-3-carboxamide.

A mixture of Lindlar catalyst (2 g) and the title compound of example (4e) (20 g, 72.7 mmol) in ethanol (160 ml) was hydrogenated for 48 hours at 345kPa (50 psi) and 50° C., then cooled and filtered. The filtrate was combined with an IMS wash (50 ml) of the filter pad and concentrated under reduced pressure to a column of 100 ml. The remaining ethanol was removed by distillation, and replaced with ethyl acetate until a head temperature of 77° C. had been achieved. The cooled mixture was granulated at 4° C., filtered and dried to afford the title compound (13.17 g, 73%) as a light brown solid. δ (DMSO$_{d6}$): 0.90 (3H,t), 2.54 (2H,q), 4.48 (2H,s), 5.31 (2H,s), 6.89 (1H,d), 6.95 (1H,s), 7.11 (1H,s), 7.28 (1H,m), 7.74 (1H,m), 8.50 (1H,d). LRMS: m/z 246 (M+1)$^+$.

PREPARATION 2

N-[3-carbamoyl-5-ethyl-1-(2-Pyridylmethyl)-1H-pyrazol-4-yl]-2-ethoxy-5-(4-ethyl-1-piperazinylsulfonyl)nicotinamide 2-Ethoxy-5-(4-ethyl-1-piperazinylsulfonyl)nicotinic acid (0.875 Kg, 2.55 mol) was charged followed by ethyl acetate (7L, 8 ml/g) to the reaction vessel and 2 ml/g was distilled off at atmospheric pressure to ensure the reaction system was dry. The slurry was cooled to room temperature under a nitrogen atmosphere and carbonyldiimidazole (0.43 Kg, 2.65 mol) added in one portion. The slurry was heated to 35° C. and held for half an hour. The reaction was further heated to 45–50° C. and held for a further half hour. The reaction was then heated to reflux, stirring at reflux for one hour. On confirmation of complete imidazolide formation the reaction was cooled to 45–50° C. under nitrogen and 4-amino-5-ethyl-1-(2-pyridylmethyl)-1H-pyrazole-3-carboxamide (0.59 Kg, 2.42 mol) charged in one portion before returning to reflux and a further 1 ml/g was distilled off at atmospheric pressure. The reaction was stirred at reflux for 16 hours with crystallisation of product occurring after 4 hours. The reaction was cooled to 10–15° C. and granulated for one hour. The reaction slurry was filtered and washed (ethyl acetate) which was dried under vacuum at 50° C. to afford the title compound (1.252 Kg, 90.7%) as a white solid. Mpt 178–179° C. ? (CDCl$_3$): 1.04 (3H, t), 1.06 (3H, t), 1.59 (3H, t), 240 (2H, q), 2.50 (4H, q), 2.90 (4H, q), 3.08 (4H, m), 2.78 (2H, q), 5.35 (1H, s) 5.48 (2H, s), 6.68 (1H, s), 6.92 (1H, d), 7.22 (IH, m), 7.65 (1H, m), 8.58 (1H, d), 8.64 (1H, d), 8.83 (1H, d). m/z (Found:571 [M+H]$^+$, 100%. C$_{26}$H$_{34}$N$_8$O$_5$S requires 571.67).

PREPARATION 3

4-{6-Ethoxy-5-[3-ethyl-6,7-dihydro-7-oxo-2-(2-pyridylmethyl)-2H-pyrazolo[4,3-d]pyrimidin-5-yl]-3-pyridylsulfonyl}-1-ethylpiperazine Potassium ethoxide solution (86 g, 0.25 mol, 24% w/w in ethanol) was charge to the vessel. To this was added ethanol (235 mL). Ethyl acetate (10.8 g) was added to reaction mixture at ambient. N-[3-carbamoyl-5-ethyl-1-(2-pyridylmethyl)-1H-pyrazol4-yl]-2-ethoxy-5-(4-ethyl-1-piperazinylsulfonyl) nicotinamide (70 g, 0.122 mol) was added in one portion to the solvent mixture and the reaction was stirred at ambient. The reaction mixture was warmed in a pressurised vessel to a temperature of 120° C., producing an internal pressure of approximately 50–60 p.s.i., the pressure was then made up to 80 p.s.i. by applying a nitrogen pressure and the reaction was stirred for 8 hours. The reaction was cooled after 8 hours and ethanol is then reduced under atmospheric distillation to a volume of about 720 ml (3 ml/g). Ethyl Acetate (840 ml) was added to the ethanol solution and then reduced under atmospheric distillation to a volume of 1920 ml (8 ml/g). Dilute aqueous hydrochloric acid was added to adjust the pH of the reaction mixture from about pH=13 to pH=8. This was a slow addition over 30 min showing no exotherm. The mixture was stirred for 5 minutes, warmed to 50° C. and the phases were separated. The aqueous was run off to the effluent. Water (140 mL) was added to ethyl acetate layer (remaining in the vessel), stirred, warmed to 50° C. and the phases were separated. The aqueous was run off to the effluent. The ethyl acetate phase was slowly cooled from 50° C. to 0–5° C. over two hours, and stirred for a further hour, filtered of the solid, wash with ethyl acetate (3) 0–5° C. and dried under vacuum at 60° C. to afford the title compound (83%) as a white solid. Mpt 178–180° C. (CDCl$_3$): 1.02 (3H, t), 1.30, 3H, t), 1.58 (3H, t), 2.21 (2H, q), 2.55 (4H, m), 3.04 (2H, q), 3.10 (4m), 4.75 (2H, q), 5.69 (2H, s), 7.10 (1H, d), 7.22 (1H, m), 7.63 (1H, m), 8.57 (1H, d), 8.63 (1H, d), 9.02 (1H, d). m/z (Found:553 [M+H]$^+$, 100%. C$_{26}$H$_{32}$N$_8$O$_4$S requires 553.66).

PREPARATION 4

(a) 2-Hydroxy-5-sulfonicotinic acid

2-Hydroxynicotinic acid (27 Kg, 194.2 mol) was added portionwise to 30% oleum (58.1 Kg) at 50° C. over 1 hr. This caused an exotherm to 82° C. The reaction mixture was heated further to 140° C. After maintaining this temperature for 12 hrs the reactor contents were cooled to 15° C. and filtered. The filter cake was then re-slurried with acetone (33 Kg) at room temperature, filtered and dried to afford the title compound (35.3 Kg, 83%) as a white solid. Decomposition pt 273° C. d (DMSO$_{d6}$): 7.93 (1H, d), 8.42 (1H, d). m/z (Found:220 [M+H]$^+$, 100%. C$_6$H$_6$NO$_6$S requires 220.17).

(b) Ethyl 2-hydroxy-5-sulfonicotinoate

2-Hydroxy-5-sulfonicotinic acid (500 g, 2.28 mol) was dissolved in ethanol (2.5L) with stirring and heated to 80° C. After 30 mins 0.5L of solvent was distilled off, then replaced with fresh ethanol (0.5L) and taken back to 80° C. After a further 60 mins 1.0L of solvent was distilled off, then replaced with fresh ethanol (1.0L) and taken back to 80° C. After a further 60 mins 1.0L of solvent was distilled off, the reaction cooled to 22° C. and stirred for 16 hr. The precipitated product was filtered, washed with ethanol (0.5L) and dried at 50° C. under vacuum to afford the title compound (416 g, 74%) as a white solid. Decomposition pt 237° C. d (DMSO$_{d6}$): 1.25 (3H, t), 4.19 (2H,q), 7.66 (1H, d), 8.13 (1H, d). m/z (Found:248 [M+H]$^+$, 100%. C$_8$H$_{10}$NO$_6$S requires 248.22).

(c) Ethyl 2-chloro-5-chlorosulfonicotinoate

Ethyl 2-hydroxy-5-sulfonicotioate (24.7 g, 0.1 mol) was slurried in thionyl chloride (238 g, 2.0 mol) and dimethylformamide (1.0 mL) with stirring. The reaction mixture was then heated to reflux for 2.5 hr. The bulk of the thionyl chloride was removed under vacuum with residual thionyl chloride removed with a toluene azeotrope to afford the crude title compound (30.7 g, 108%) as a yellow oil. d (CDCl$_3$): 1.46 (3H, t), 4.50 (2H, q), 8.72 (1H, d), 9.09 (1H, d). This was taken directly onto the next step.

(d) Ethyl 2-chloro-5-(4-ethyl-1-piperazinylsulfonyl) nicotinoate

Crude ethyl 2-chloro-5-chlorosulfonicotinoate (30.7 g, 0.1 mol assumed) was dissolved in ethyl acetate (150 mL) with stirring then ice cooled. To this was added a solution of N-ethylpiperazine (11.4 g, 0.1 mol) and triethylamine (22.5 g, 0.22 mol) in ethyl acetate (50 mL), carefully over 30 mins, keeping the internal temperature below 10° C. Once the addition was complete the reaction was allowed to warm to 22° C. and stir for 1 hr. The solid was filtered off and the remaining filtrate was concentrated under vacuum to afford the crude title compound (37.1 g, 103%) as a crude yellow gum. d (CDCl$_3$): 1.10 (3H, t), 1.42 (3H, m), 2.50 (2H, m), 2.60 (4H, m), 3.19 (4H, m), 4.43 (2H, q) 8.40 (1H, d), 8.80

(1H, d). m/z (Found:362 [M+H]⁺, 100%. C₁₄H₂₁ClN₃O₄ requires 362.85).

(e) Ethyl 2-ethoxy-5-(4-ethyl-1-piperazinylsulfonyl) nicotinoate

A solution of Ethyl 2-chloro-5-(4-ethyl-1-piperazinylsulfonyl)nicotinoate (36.1 g, 0.1 mol) in ethanol (180 mL) was cooled to 10° C. with stirring. Sodium ethoxide (10.2 g, 0.15 mol) was added portionwise keeping the temperature below 20° C. The reaction mixture was then stirred at ambient temperature for 18 hours. The precipitate was filtered off and water (180 mL) added to the filtrate. The filtrate was then heated to 40° C. for 1 hour. Ethanol (180 mL) was then distilled off at ambient pressure and the remaining aqueous solution allowed to cool to ambient temperature. The precipitated product was then filtered off, washed with water and dried under vacuo at 50° C. to afford the title compound (12.6 g, 34%) as a light brown solid. M.p. 66–68° C. d (CDCl₃): 1.04 (3H, t), 1.39 (3H, t), 1.45 (3H, t), 2.41 (2H, q), 2.52 (4H, m), 3.08 (4H, m), 4.38 (2H, q), 2.57 (2H, q), 8.38 (1H, d), 8.61 (1H, d). m/z (Found:372 [M+H]⁺, 100%. C₁₆H₂₆N₃O₅S requires 372.46).

(f) 2-Ethoxy-5-(4-ethyl-1-piperazinylsulfonyl) nicotinic acid

Ethyl 2-ethoxy-5-(4-ethyl-1-piperazinylsulfonyl) nicotinoate (10.2 g, 0.0275 mol) was dissolved in toluene (50 mL) and a solution of sodium hydroxide (1.1 g, 0.0275 mol) in water (20 mL) added to it. This two phase mixture was then stirred vigorously at ambient temperature overnight. The aqueous phase was separated off and adjusted to pH=5.6 by addition of c. hydrochloric acid. The precipitated product was slurried with ice cooling for 15minutes, filtered, water washed and dried under vacuo at 50° C. to afford the title compound (4.1 g, 43%) as an off-white solid. Mpt 206–207° C. d (CDCl₃): 1.25 (3H, t), 1.39 (3H,t), 2.82 (2H, q), 3.03 (4H, m), 3.25 (4H, m), 4.50 (2H, q), 8.25 (1H, d), 8.56 (1H, d). m/z (Found:344 [M+H]⁺, 100%. C₁₄H₂₂N₃O₅S requires 344.38).

What is claimed is:

1. An anhydrous para-toluenesulphonic acid salt of 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo [4,3-d]pyrimidin-7-one having the formula (I);

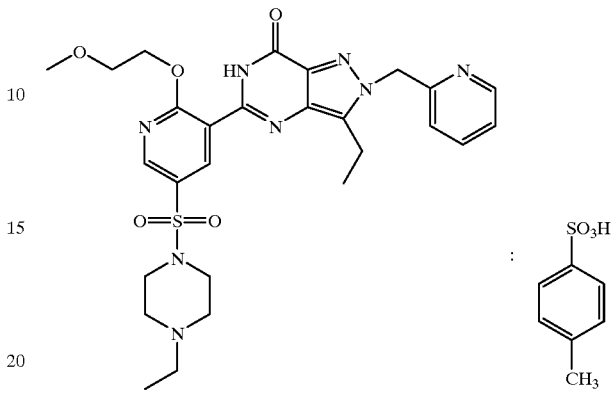

2. A salt according to claim 1 having a melting point of 240° C. ±5° C.

3. A pharmaceutical composition containing a salt according to claim 1 together with a pharmaceutically acceptable diluent or carrier.

4. A pharmaceutical composition according to claim 3 which is adapted for oral treatment.

5. A process for the preparation of a salt according to claim 1 from 4-{6-Ethoxy-5-[3-ethyl-6,7-dihydro-7-oxo-2-(2-pyridylmethyl)-2H-pyrazolo [4,3-d]pyrimidin-5-yl]-3-pyridylsulfonyl}-1-ethylpiperazine via treatment with para-toluenesulphonic acid monohydrate.

6. A process according to claim 5 wherein the ratio molar equivalents of 4-{6-Ethoxy-5-[3-ethyl-6,7-dihydro-7-oxo-2-(2-pyridylmethyl)-2H-pyrazolo [4,3-d]pyrimidin-5-yl]-3-pyridylsulfonyl}-1-ethylpiperazine to para-toluenesulphonic acid is about 1:1.

* * * * *